(12) United States Patent
Fu

(10) Patent No.: US 6,348,500 B1
(45) Date of Patent: Feb. 19, 2002

(54) USES OF MODAFINIL AND ITS D/L ENANTIOMERS

(76) Inventor: Junchang Fu, Room 901, Bldg. 12, Fang Chen Yuan Area 3, Fang Zhuang, Fengtai District, Beijing (CN), 100078

( * ) Notice: Subject to any disclaimer, the term of this patent is extended or adjusted under 35 U.S.C. 154(b) by 0 days.

(21) Appl. No.: 09/553,608

(22) Filed: Apr. 20, 2000

(30) Foreign Application Priority Data

Sep. 29, 1999 (CN) .......................... 99119726 A

(51) Int. Cl.⁷ .................. A61K 9/20; A61K 31/165; A61K 8/48; A61P 15/08
(52) U.S. Cl. .................. 514/618; 424/451; 424/464
(58) Field of Search .................. 514/618; 424/449, 424/451, 464, 489

(56) References Cited

U.S. PATENT DOCUMENTS 4,177,290 A 12/1979 Lafon .................. 424/324

OTHER PUBLICATIONS

B. Saletu, et al., "Differential Effects of the New Central Adrenergic Agonist Modafinil and d–Amphetamine on Sleep and Early Morning Behavior in Elderlies", Arancim–Forsch./Drug Res. 39(II), No. 10, p. 1268 (1989).

*Primary Examiner*—Edward J. Webman
*Assistant Examiner*—Helen Nguyen
(74) *Attorney, Agent, or Firm*—Darby & Darby

(57) ABSTRACT

This invention relates to new uses of Modafinil and its D/L enantiomers, particularly the new uses in the pharmaceutical preparation field. This invention provides new uses of Modafinil and its D/L enantiomers in preparing the medicine for increasing and enhancing the quantity and quality of normal spermatozoa in male mammals, the medicine for enhancing the pregnant capacity in female mammals, the medicine for treating infertility, subfertility and sex dysfunction in male and female mammals, and the medicine for enhancing the sexual function in mammals.

24 Claims, No Drawings

USES OF MODAFINIL AND ITS D/L ENANTIOMERS

TECHNICAL FIELD OF THE INVENTION

This invention relates to new uses of Modafinil and its D/L enantiomers, particularly the new uses in the pharmaceutical preparation field. This invention provides new uses of Modafinil and its D/L enantiomers in preparing the medicine for increasing and enhancing the quantity and quality of normal spermatozoa in male mammals, the medicine for enhancing the pregnant capacity in female mammals, the medicine for treating infertility, subfertility and sex dysfunction in male and female mammals, the medicine for enhancing the sexual function in mammals.

BACKGROUND OF THE INVENTION

As stated in the U.S. Pat. No. 4,177,290, Modafinil is a known chemical. The chemical name of Modafinil is:

2-[(Diphenylmethyl) sulfinyl]-N-Acetamide The structure of Modafinil is shown as follows:

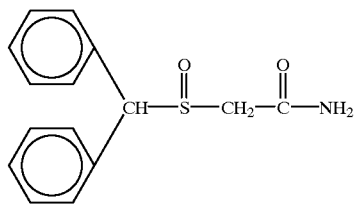

Modafinil's formula is $C_{15}H_{15}NO_2S$ and the molecular weight is 273.35, which is insoluble in water and cyclohexane, sparingly or slightly soluble in methanol and acetone. Modafinil and its D/L enantiomers are white or whitish crystals. The racemic compound has a melting point of 163–165° C. The racemic compound and both of the enantiomers have the same characteristics stated above.

As published in Proceedings of the Meeting of the $5^{th}$ International Congress of Sleep Research, p.470. European Sleep Research Society. Jun. 28–Jul. 3, 1987, Copenhagen. Modafinil is a vigilance-inducing agent used in the treatment of paroxysmal narcolepsy and idiopathic hypersomnia. Modafinil and its D/L enantiomers have been eligible for marketing in Great Britain, France and USA, mainly used for treating paroxysmal narcolepsy and idiopathic hypersomnia. No reports regarding the new use of Modafinil as a medicine for enhancing reproductive or sexual ability as stated in this document have been found in the literature.

BRIEF DESCRIPTION OF THE INVENTION

The purpose of this invention is to provide new uses of Modafinil and its D/L enantiomers in preparing the medicine for increasing and enhancing the quantity and quality of normal spermatozoa in male mammals, the medicine for enhancing the pregnant capacity in female mammals, the medicine for treating infertility, subfertility and sex dysfunction in male and female mammals, the medicine for enhancing the sexual function in mammals.

DETAILED DESCRIPTION OF THE INVENTION

The preparation of Modafinil consists of many steps, e.g. reaction of diphenyl-methanol and thiourea and chloroacetic acid, and then oxidation and amidation, etc. The detailed methodology in the Example 1 is referred to the methodology of Example 1 in the U.S. Pat. No. 4,177,290.

In the following, 3 examples of pharmacological experiments in rats are described. As rat is a kind of mammal close to human being, the effects of Modafinil in rats can be deduced to have the same effects in human beings.

EXAMPLE 1

THE EFFECT OF MODAFINIL ON SPERMATOGENESIS

EXPERIMENTAL ANIMALS: SD male rats, 2 months old, weighing 210 to 260 g, were used for this experiment. All the animals were fed in the laboratory for a week before starting the experiment for accommodative purpose. The animals were distributed randomly into 5 experimental groups, 10 in each group. The room temperature was kept at 20 to 25° C. 4 groups of rats were administrated with Modafinil and 1 group for control.

METHODS AND PROTOCOLS: In treated groups, various doses of Modafini were given by gavage as 200, 400, 600 and 800 mg/kg/day in rats. Modafinil(prepared according to Example 1 in the U.S. Pat. 4,177,290) was mixed with 3% starch paste, 2ml for each rat per day, gavage feeding for successive 30 days. The controlled animals received 5 the 3% starch paste without drug, with same amount for 30 successive days. The morphology, motility and number of the spermatozoa of the animals in each group were observed and counted. On days 31, all animals were killed. Spermatozoa in the sperm taken from epididymis tail were counted; the testes and prostates were taken out. Histological sections were made and examined under microscope.

RESULTS: In rats of all the Modafinil treated groups, number of spermatozoa remarkably increased with active motility. (Table 1)

TABLE 1

Effect of Modafinil on spermatozoa counts in rats
(mean number of spermatozoa per gram weight of sperm ± S.D.)

| Control | Modafinil treated (mg/kg/day) | | | |
|---|---|---|---|---|
| 0 | 200 | 400 | 600 | 800 |
| 487.5 ± 310.5 | 819.8 ± 295.6 | 1753.8 ± 540.6 | 1706.0 ± 379.9 | 1656.0 ± 165.8 |

The above differences between the Modafinil treated groups and the controls were very statistically significant. Histological examinations proved that in the groups treated with Modafinil, stages of normal spermatogensis in the seminiferous tubules were more distinct and regular than those in the controls. All the tubule cavities were extremely full of countless maturing normal spermatozoa. No cell degeneration was found during the course of spermatogensis and the synchronous meiotic pictures were clearly seen without any morphologically abnormality.

CONCLUSION: Modafinil and its enantiomers have strong effect of enhancing spermatogensis in male mammals to increase the normally matured and more active spermatozoa.

EXAMPLE 2

THE EFFECT OF MODAFINIL ON SEXUAL ABILITY

EXPERIMENTAL ANIMALS: SD rats of both sexes were used and feeding methods of the drug were the same as in the Example 1.

EXPERIMENTAL PROTOCOL: 15 males and 15 females for control fed with 3% starch paste for 15 days while 15 males and 15 females were treated with 200 mg/kg/day of Modafinil(prepared according to Example 1 in the U.S. Pat. No. 4,177,290) for 15 days. On day 16 evening, each special cage was distributed by chance with 1 male and 1 female rat couple. For the first 2 hours of cohabitation, the numbers of sexual intercourse movement of male along with acceptance of female were counted.

EXPERIMENTAL RESULT: In the treated group, the number of sexual intercourse was $5.0\pm1.2$ times (Mean±S.D.)/2 hours/couple while that in the control group showed $3.1\pm0.9$ times. The mean number in the treated group was 161% of the control.

CONCLUSION: The number of sexual intercourse in the Modafinil-treated rats was significantly higher than that in controls.

EXAMPLE 3

THE EFFECT OF MODAFINIL ON UTERUS WEIGHT IN FEMALE RATS

EXPERIMENTAL ANIMAL: Young female SD rats of 25 days old were used. Food and drug administration was the same as used in the Example 1.

EXPERIMENTAL PROTOCOL: 15 female rats for control were fed 3% starch paste 2ml/day for 15 successive days. 15 female rats treated with Modafinil(prepared according to Example 1 in the U.S. Pat. No. 4,177,290) mixed with 3% starch paste for 200 mg/kg/day in 2 ml of is starch paste a day. Animals were sacrificed on day 16 and the uterei were taken out. Every fresh uterus was weighed.

EXPERIMENT RESULT. The mean uterus weight of the, treated rats was $0.418\pm0.082$ g (Mean±S.D.) while that in the controls were $0.265\pm0.057$ g. The mean uterus weight of the treated rats equals 158% of that in controls.

CONCLUSION: Modafinil and its D/L enantiomers increase the uterus weight remarkably, that improves the pregnant capacity of the uterus.

ADMINISTRATION AND DOSAGE: By routine methods, Modafinil and its D/L enantiomers are made into tablets or capsules for oral use (effects in tablets or capsules are the same). The dose for an adult is suggested as 200–400 mg divided into 1–2 times a day.

What is claimed is:

1. A method for increasing the spermatozoa count in a male mammal comprising the step of administering modafinil to the male mammal.

2. The method of claim 1, wherein the D-enantiomer of modafinil is administered.

3. The method of claim 1, wherein the L-enantiomer of modafinil is administered.

4. The method of claim 1, wherein a mixture of the D and L enantiomers of modafinil is administered.

5. A method for increasing the fertility of a female mammal comprising the step of administering modafinil to the female mammal.

6. The method of claim 5, wherein the D-enantiomer of modafinil is administered.

7. The method of claim 5, wherein the L-enantiomer of modafinil is administered.

8. The method of claim 5, wherein a mixture of the D and L enantiomers of modafinil is administered.

9. A method for treating infertility in a female mammal in need thereof comprising the step of administering modafinil to the female mammal.

10. The method of claim 9, wherein the D-enantiomer of modafinil is administered.

11. The method of claim 9, wherein the L-enantiomer of modafinil is administered.

12. The method of claim 9, wherein a mixture of the D and L enantiomers of modafinil is administered.

13. A method for increasing the sexual activity of a mammal comprising the step of administering modafinil to the mammal.

14. The method of claim 13, wherein the D-enantiomer of modafinil is administered.

15. The method of claim 13, wherein the L-enantiomer of modafinil is administered.

16. The method of claim 13, wherein a mixture of the D and L enantiomers of modafinil is administered.

17. A method for treating sexual dysfunction in a mammal in need thereof comprising the step of administering modafinil to the mammal.

18. The method of claim 17, wherein the D-enantiomer of modafinil is administered.

19. The method of claim 17, wherein the L-enantiomer of modafinil is administered.

20. The method of claim 17, wherein a mixture of the D and L enantiomers of modafinil is administered.

21. The method of claim 1, wherein the male mammal is a human being.

22. The method of claim 2, wherein the male mammal is a human being.

23. The method of claim 3, wherein the male mammal is a human being.

24. The method of claim 4, wherein the male mammal is a human being.

* * * * *